United States Patent
Sawyer et al.

(10) Patent No.: US 6,562,621 B1
(45) Date of Patent: May 13, 2003

(54) METHOD OF USING FISH OVARIAN FLUID FOR CULTURE AND PRESERVATION OF MAMMALIAN CELLS

(75) Inventors: Evelyn S. Sawyer, Arundel, ME (US); Philip J. Sawyer, Arundel, ME (US); Paul A. Janmey, Arundel, ME (US)

(73) Assignee: Sea Run Holdings, Inc., Freeport, ME (US)

(*) Notice: Subject to any disclaimer, the term of this patent is extended or adjusted under 35 U.S.C. 154(b) by 0 days.

(21) Appl. No.: 09/697,598

(22) Filed: Oct. 27, 2000

Related U.S. Application Data

(60) Provisional application No. 60/161,912, filed on Oct. 28, 1999.

(51) Int. Cl.$^7$ ................................................. C12N 5/00
(52) U.S. Cl. ........................... 435/408; 435/1.1; 435/2; 435/374; 435/391; 424/537; 424/559
(58) Field of Search ................................. 435/408, 391, 435/374, 1.1, 2; 424/537, 559

(56) References Cited

U.S. PATENT DOCUMENTS

| | | | |
|---|---|---|---|
| 4,647,552 A | * 3/1987 | Gulyas et al. | |
| 5,401,653 A | 3/1995 | Sawyer et al. | |
| 5,426,045 A | 6/1995 | Sawyer et al. | |
| 6,207,817 B1 | * 3/2001 | Wu et al. | |

OTHER PUBLICATIONS

Coffman, et al.; Trout Ovulatory Proteins are Partially Responsible for the Anti-Proteolytic Activity Found in Trout Coelomic Fluid; Department of Biological Sciences, University of Notre Dame; Apr. 14, 1998; pp. 497–502.

Hirano, et al.; Changes in Plasma and Coelomic Fluid Composition of the Mature Salmon (Oncorhynchus Keta) During Freshwater Adaptation; Ocean Research Institute, University of Tokyo; Jan. 1978; pp. 5–8.

Kanamori, et al.; Isolation and Characterization of Deaminated Neuraminic Acid–Rich Glycoprotein (KDN–gp–OF) in the Ovarian Fluid of Rainbow Trout (Salmo Gairdneri); *Biochemical and Biophysical Research Communications*; Oct. 1989; vol. 164 No. 2 pp 744–749.

Reid, et al.; Symposium on Cryopreservation of Human Platelets: An Overview; *Cryobiology*; 1999; pp. 177–179.

Song, et al.; Structure of Novel Gangliosides, Deaminated Neuraminic Acid (KDN)–Containing Glycosphingolipids, Isolated from Rainbow Trout Ovarian Fluid; American Chemical Society; 1993; pp. 9221–9229.

Tablin, et al.; Membrane Phase Transition of Intact Human Platelets: Correlation with Cold–Induced Activation; *Journal of Cellular Physiology*; Feb. 1996; pp 305–313.

Will, et al.; Creutzfeldt–Jakob Disease and the Risk from Blood or Blood Products; *VoxSanguinis*; Mar. 1998; pp. 17–180.

Reglero, et al.; Polysialic Acids; *J. Biochem*; 1993; pp 1517–1527.

Huang, et al.; A Protease Inhibitor of the Serpin Family is a Major Protein in Carp Perimeningeal Fluid: I. Protein Purification and Characterization; *Journal of Neurochemistry*; 1995; pp. 1715–1720.

* cited by examiner

Primary Examiner—Leon B. Lankford, Jr.
(74) Attorney, Agent, or Firm—IP Strategies, PC

(57) ABSTRACT

A method of using fish ovarian fluid for culture and preservation of mammalian cells includes obtaining ovarian fluid from a fish, and culturing mammalian cells in media including a commercially defined medium and a nutrient medium, wherein the nutrient medium includes the fish ovarian fluid. The cells may initially be cultured in a commercial medium and a conventional nutrient medium prior to culture in the fish ovarian fluid. Living cells may also be preserved by obtaining ovarian fluid from a fish, isolating the living cells, and adding the fish ovarian fluid to the living cells.

3 Claims, 3 Drawing Sheets

NIH 3T3 FIBROBLASTS GROWN
20 HR IN 10% CALF SERUM,
90% DMEM

NIH 3T3 FIBROBLASTS GROWN
20 HR IN 100% TROUT
OVARIAN FLUID

HIGHER MAGNIFICATION VIEW
OF FIBROBLASTS IN 100%
OVARIAN FLUID UNDERGOING
CELL DIVISION

M2 MELANOMA CELLS GROWN
36 HOURS IN 10% CALF SERUM,
90% MEM

M2 MELANOMA CELLS GROWN
36 HOURS IN 5% CALF SERUM,
50% TROUT OVARIAN FLUID,
AND 45% MEM

HIGHER MAGNIFICATION OF
SINGLE M2 CELL GROWN
70 HRS IN 100% TROUT
OVARIAN FLUID

PLATELETS IN PFP
COOLED TO 4°C FOR 1 HR

PLATELETS IN 90% PFP
10% OVARIAN FLUID
COOLED TO 4°C FOR 1 HR

METHOD OF USING FISH OVARIAN FLUID FOR CULTURE AND PRESERVATION OF MAMMALIAN CELLS

CLAIM OF PRIORITY

A right of priority under 35 USC §119 is claimed from U.S. Provisional Patent Application No. 60/161,912, which was filed on Oct. 28, 1999 and the entire disclosure of which is incorporated herein by reference.

FIELD OF THE INVENTION

The present invention relates generally to the culture and preservation of cells, and more specifically to the culture and preservation of mammalian cells using the ovarian fluid produced by spawning fish. The method has significant advantages over conventional methods, which use whole serum or plasma components derived from mammals or fish.

BACKGROUND OF THE INVENTION

The culture of animal cells requires a defined medium containing a specific quantity of certain chemicals, and for the culture of most mammalian cells, an undefined nutrient supplement (medium) is also required. From the earliest attempts at cell culture to the present, this nutrient medium has been derived exclusively from animal or human blood. Fetal bovine serum (FBS) remains the most common nutrient medium used for the culture of animal cells. However, in order to eliminate certain risks, and to better quantify media components, a recent trend is to use so-called "serum-free" media. These formulations are not truly serum-free, but rather contain specific quantities of certain serum or plasma components, such as albumin or lipids, in place of whole serum.

This reliance on the use of blood components as nutrients in mammalian cell culture has led to an increased concern over the presence of possible infectious agents in the cells. For example, problems remain in achieving 100% viral inactivation in blood products without compromising quality. An equally serious concern is the emergence of transmissable spongiform encephalopathies (TSEs) in mammalian blood and plasma components. The latter problem is especially difficult to overcome, since at present it is not possible to predict which donors, animal or human, will later develop a prion disease. Although some plasma proteins can be produced by recombinant technology, others, such as many glycoproteins, cannot. In addition, recombinant proteins are generally very expensive.

In order to reduce the risks from mammalian infectious agents, a whole serum product has been developed from fish, particularly salmon and trout, for mammalian and insect cell culture. Although this material is a satisfactory substitute for FBS in a few cell lines, its usefulness is limited by high levels of non-protein nitrogen (NPN), by large amounts of lipids that are easily oxidized, and especially, by proteases that are active at 4° C. The latter problem contraindicates the use of salmonid serum as a medium for preservation and storage of cells at low temperature.

In addition to fish whole serum for mammalian cell culture, fish plasma components, specifically antifreeze glycoproteins (AFGPs) from polar fishes, have been used successfully in low temperature preservation of cells such as human platelets. Although these AFGPs appear promising, their availability is severely limited by the relatively small numbers and size of polar fishes, their natural source, and the difficulty of producing the recombinant glycoprotein.

There is therefore a great need for a nutrient medium that overcomes or minimizes the foregoing problems, and which is also practical for widespread use.

SUMMARY OF THE PRESENT INVENTION

While the field of cell culture has recently come to include blood products from fish, the ovarian fluid of fish has been of interest only to those in fishery science. The ovary of salmonid fishes lacks an ovarian membrane, and ovulated eggs are free in the body cavity surrounded by the slightly viscous fluid. At spawning, the eggs and ovarian fluid are expelled through the genital pore. Ovarian fluid has been studied for its role in salmonid reproduction and for its chemical composition, its novel proteins, and its utility in testing for the presence of fish disease.

According to the present invention, this ovarian fluid produced by spawning female salmon or trout is used to replace whole serum or plasma components as a nutrient medium in mammalian cell culture. The use of this substance as a nutrient medium in the place of whole serum or plasma components promotes the growth and proliferation of the mammalian cells (for example, NIH 3T3 and M2 cells). Use of fish ovarian fluid eliminates the risks and uncertainties inherent in the use of mammalian blood products, as well as the limiting factors of NPN, lipids, and proteases associated with fish serum or plasma when used as nutrient media.

Further, according to the present invention, salmonid ovarian fluid is used in low-temperature preservation of mammalian cells, especially human platelets. With present technology, these cells must be stored at or above 22° C., as lower temperatures produce "activation", that is, a process marked by aggregation and change in shape, and resulting in irreversible cellular damage. Storage at 4° C. could dramatically increase the useful life of the mammalian cells, now limited to less than a week at 22° C.

Several factors have hindered, or have led those of skill in the art away from, the previous use of fish ovarian fluid for mammalian cell culture and preservation. For example, the field of cell culture and storage, including platelet preservation, is distinctly different from the field of fishery science; those skilled in working with mammalian cells would be unlikely to know of the existence of ovarian fluid and therefore could not speculate on its utility. Certainly, there has been no suggestion to motivate those working with mammalian cells to expend the time, effort, and expense necessary to experiment with fish ovarian fluid to culture or preserve mammalian cells.

Further, utilization of blood products as the nutrient supplements in mammalian cell culture is firmly established. Use of a nutrient fluid from a source other than blood would appear unlikely to be advantageous to one skilled in the art of animal cell culture, particularly absent of any suggestion by those in the field of an advantage.

In addition, the presence of ovarian fluid in wild fish is relatively brief and seasonal, unlike that of blood. Also, spawning time in wild fish under natural conditions varies among stocks and individual fish. These and other factors make it logistically difficult to obtain practically usable quantities of ovarian fluid from wild fish.

Salmonid ovarian fluid contains very small amounts of the components generally considered essential for cell growth, and therefore would appear to be a poor choice for a nutrient medium. For example, the standard nutrient medium FSB contains about 4 g/dL protein and 40 mg/dL cholesterol. Similarly, salmonid serum contains about 4 g/dL protein and more than 200 mg/dL cholesterol. A representative sample of pooled ovarian fluid has been analyzed and was found to contain only 0.2 g/dL total protein and 6 mg/dL cholesterol. It also has been found that ovarian fluid from chum salmon contained only about 10% of the protein and cholesterol found in the plasma. Known and hypothesized functions of ovarian fluid include protection of the eggs from physical or osmotic damage, and maintenance of sperm motility. These functions do not suggest a role for ovarian fluid in mammalian cell culture or preservation.

The use of blood products from the coldwater fishes for mammalian cell culture or storage offers safety from mammalian infectious agents. However, and despite the indications otherwise, it has been found in the extensive research leading to the development of the present invention that the use of ovarian fluid from these fish provides significant advantages over the use of fish blood products.

For example, analyses of salmonid ovarian fluid show very low levels of NPN, lipids and protease activity, factors that have proven inhibitory in the use of fish serum for culture or preservation of mammalian cells.

Further, Salmonid ovarian fluid contains protease inhibitors. As a result of the research, it has been determined that trout ovarian fluid contains a thrombin inhibitor, and antiproteolytic activity has been observed in fish ovarian fluid.

In addition, ovarian fluid can be obtained from farmed salmonids in at least twice the quantity of serum. Only about 50 ml of serum (100 mls of whole blood) can be obtained from even the largest (5–6 kg) farmed salmon, but a 2–4 kg fish can produce 100 mls of ovarian fluid. This large volume of ovarian fluid was also noted in trout. Farmed fish also provide ovarian fluid that is more consistent than that of wild fish, leading to more reproducible results.

As part of the research it was also found that salmonid ovarian fluid contains components similar to those involved in critical cell functions, but not identical to those provided by animal serum and plasma components. The polysialic acids are involved in organogenesis and cell adhesion and growth. Salmonid ovarian fluid contains a polysialic acid, deaminated neuraminic acid (KDN). This neuraminic acid is found in a KDN-rich glycoprotein and KDN-containing glycosphingolipids of trout ovarian fluid.

Thus, according to an aspect of the present invention, a method of using fish ovarian fluid for culture and preservation of mammalian cells includes obtaining ovarian fluid from a fish; culturing mammalian cells in first media including a first commercially defined medium and a first nutrient medium; removing the mammalian cells from the first media; replating the mammalian cells in second media including a second commercially defined medium and a second nutrient medium including the fish ovarian fluid; and continuing to culture the cells.

According to another aspect of the present invention, a method of using fish ovarian fluid for culture and preservation of mammalian cells includes obtaining ovarian fluid from a fish, and culturing mammalian cells in media including a commercially defined medium and a nutrient medium, wherein the nutrient medium includes the fish ovarian fluid.

According to still another aspect of the present invention, a method of preserving living cells includes obtaining ovarian fluid from a fish, isolating the living cells, and adding the fish ovarian fluid to the living cells.

DETAILED DESCRIPTION OF THE INVENTION

Ovarian fluid may be obtained by squeezing unfertilized eggs and accompanying fluid out of female fish into a clean container, and then separating eggs from fluid, for example by using a 1 mm nylon mesh cloth. The ovarian fluid then may be filtered, preferably through $0.45\mu$ and $0.2\mu$ sterile membrane filters, and frozen at $-80°$ C. for future use.

A. Cell Culture

In general, fish ovarian fluid may be used as at least part of the nutrient medium in cell culture at various points in the process and to various degrees. For example, mammalian cells may be grown first in a commercial defined medium and a conventional nutrient medium, which may include animal serum or plasma components, as well as other nutrients, such as glucose. After an appropriate time, the cells may be removed, cleaned of media, and replated in commercial defined medium with fish ovarian fluid as a nutrient medium. Cell culture then continues.

Alternatively, the cells may be cultured, either initially or at a later point, in a commercial defined medium with a nutrient medium composed at least in part of fish ovarian fluid. That is, the nutrient medium may include fish ovarian fluid in addition to animal serum or plasma components. The proportion of conventional medium to fish ovarian fluid may vary, depending on the particular application. Any proportion in the range of minimal fish ovarian fluid to 100% fish ovarian fluid is contemplated for a nutrient medium used in the method of the invention Two cell lines, NIH 3T3 mouse kidney fibroblasts and M2 human melanoma cells, were tested for their ability to grow in culture media containing substantial portions of trout ovarian fluid. These cell lines will be used in the following description; however, the present invention is not limited to the applications of culture of these cell lines.

NIH 3T3 cells were grown to confluence at 37° C. on tissue culture plates in Dulbecco's Modified Eagle Media (D-MEM) containing 4.5 mg/ml glucose and 10% calf serum. M2 cells were similarly grown to confluence in Minimum Essential Media with Earles salts (MEM) and 1 mg/ml glucose, 8% calf serum, and 2% FBS. The cells were then removed from the culture dish by trypsin treatment, washed, and replated at 20% confluence in media with various fractions of fish ovarian fluid in place of conventional culture media.

Figure 1A:
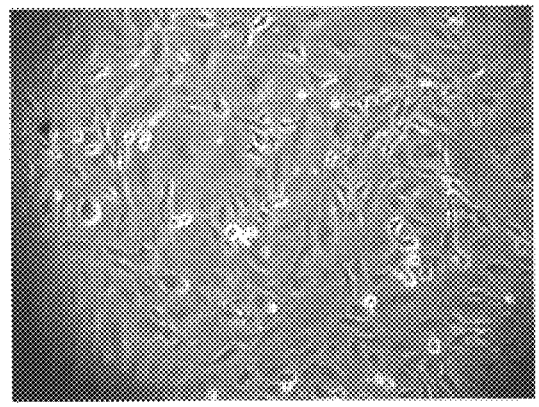
FIG. 1A shows a micrograph of cells grown in a medium containing calf serum.
Figure 1B:
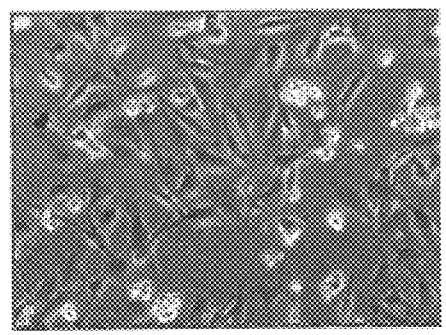
FIG. 1B shows a micrograph of cells grown in a medium containing fish ovarian fluid.
Figure 1C:
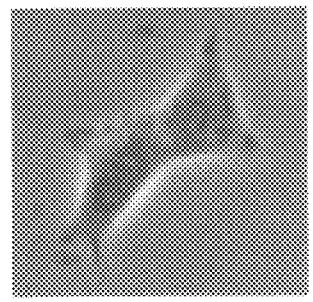
FIG. 1C shows exemplary fibroblasts after 20 hours in 10% fish ovarian fluid.

FIG. 1 shows micrographs of NIH 3T3 cells grown in media containing either calf serum or fish ovarian fluid. FIG. 1A shows control fibroblasts grown for 20 hours after plating in the control medium (D-MEM) and 10% fetal calf serum. FIG. 1B shows fibroblasts trypsinized at the same time as the controls of 1A but plated in 100% fish ovarian fluid and grown for 20 hours. FIG. 1C shows an example of fibroblasts apparently undergoing cytokinesis after 20 hours in 100% fish ovarian fluid, confirming that cell growth and division can take place in this medium. These fibroblasts remained viable in 100% fish ovarian fluid for at least 4 days without change of medium, at which time the cells became confluent. Time-lapse video microscopy confirms that these cells remain motile, and exhibit membrane ruffling protrusions characteristic of cells grown in serum-containing media.

Figure 2A:
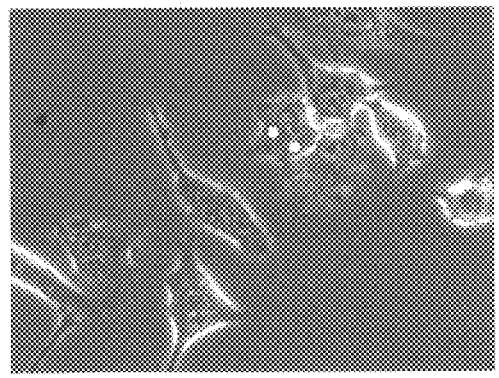
FIG. 2A shows cells grown for 36 hours in a medium containing calf serum.
Figure 2B:
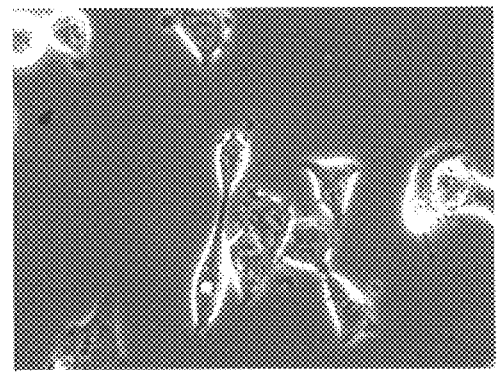
FIG. 2B shows the cells of FIG. 2A, with 50% of the medium replaced by fish ovarian fluid.
Figure 2C:
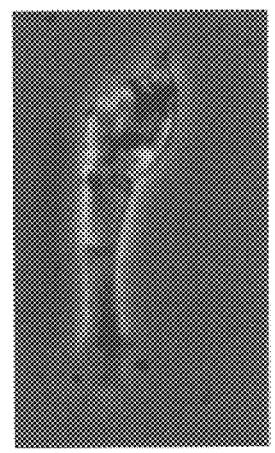
FIG. 2C shows viable cells after 70 hours in 100% fish ovarian fluid.

FIG. 2 shows another cell type M2 human melanoma grown for 36 hours in medium containing calf serum (FIG. 2A), and with 50% of the medium replaced by fish ovarian fluid (FIG. 2B). Comparison of FIGS. 2A and 2B shows that these cells, which are normally much less robust than NIH 3T3 fibroblasts, can also be maintained in substantial portions of fish ovarian fluid. These cells did not remain adherent to the plates in 100% fish ovarian fluid, probably due to adhesion factors such as fibronectin present in serum, but absent in fish ovarian fluid. However, the occasional melanoma cell that attached to the surface remained viable for at least 70 hours in 100% fish ovarian fluid, as shown in FIG. 2C. Time lapse video microscopy confirms that these cells remain motile, and exhibit surface protrusions characteristic of cells grown in serum-containing media.

B. Cell (Platelet) Preservation

In general, living cells, such as human platelets, may be preserved and protected from activation, particularly at cold (below 22° C.) temperatures, by adding fish ovarian fluid to the cells, or to a composition including the cells. The proportion of fish ovarian fluid to preserved cells may vary; the optimum ratio may be determined for each particular application. Once the fish ovarian fluid is added to the cells, the fluid/cell composition may be stored at a low temperature.

In developing the present invention, human platelets were isolated as platelet rich plasma (PRP) by standard methods using low-speed centrifugation of blood anticoagulated in acid citrate dextrose buffer (ACD). Fish ovarian fluid was added at a 1:9 volume ratio to one aliquot of PRP. To test for protection against cold activation (an indicator of platelet preservation), PRP, with or without 10% fish ovarian fluid, was cooled to 4° C. for one hour, and then re-warmed to 25° C. for 1 minute before visualization of platelets by phase-contrast microscopy. To quantify the images, unlabeled images were categorized by an observer as 1) single discoid cells; 2) single irregularly shaped activated cells; and 3) clusters of aggregated cells.

Figure 3A:
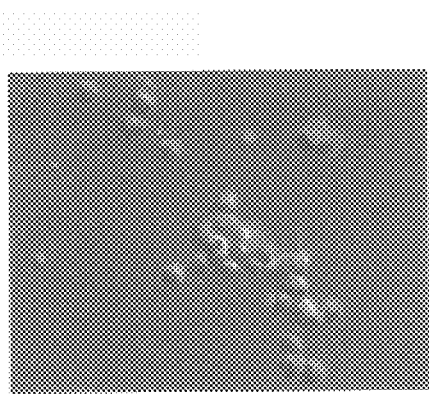
FIG. 3A shows platelets cooled and rewarmed as PRP.
Figure 3B:
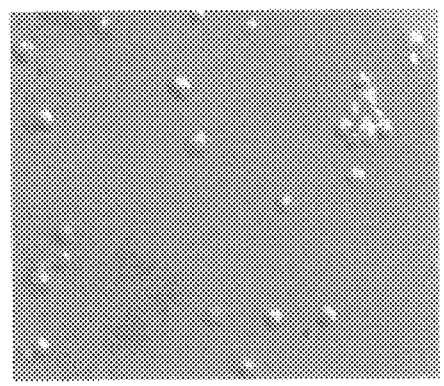
FIG. 3B shows the platelets of FIG. 3A to which 10% fish ovarian fluid is added prior to cooling.
Figure 3C:
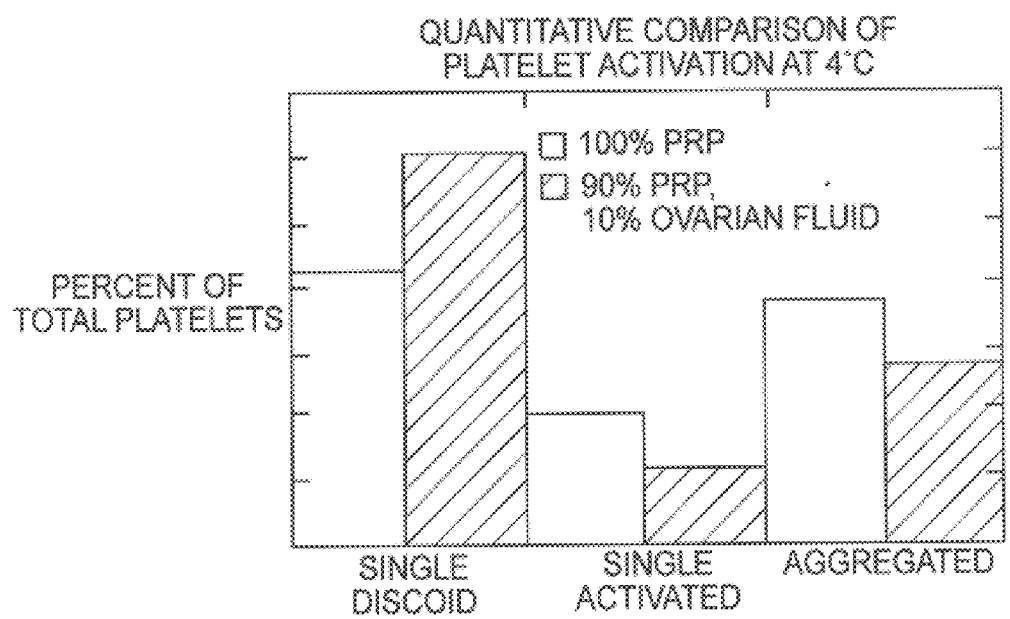
FIG. 3C shows a quantitative analysis of subject platelet images.

FIG. 3 shows how fish ovarian fluid protects human platelets against activation by low temperature. Representative images of platelets that were cooled and re-warmed as PRP (FIG. 3A) are compared to images of cells from the same sample in which 10% fish ovarian fluid was added to the PRP before cooling (FIG. 3B). FIG. 3C shows the quantitative analysis of more than 100 images of platelets taken from such micrographs, verifying that a substantial protection from cold-induced shape change and aggregation is conferred by 10% fish ovarian fluid.

Preferred and alternative embodiments have now been described in detail. It is contemplated, however, that various modifications of the disclosed embodiments fall within the spirit and scope of the invention. The scope of the appended claims, therefore, should be interpreted to include such modifications, and is not limited to the particular embodiments disclosed herein.

What is claimed is:

1. A method of using fish ovarian fluid for culture and preservation of mammalian cells, comprising:

obtaining ovarian fluid from a fish;

culturing mammalian cells in first media including a first commercially defined medium and a first nutrient medium;

removing the mammalian cells from the first media;

replating the mammalian cells in second media including a second commercially defined medium and a second nutrient medium including the fish ovarian fluid; and continuing to culture the cells.

2. A method of using fish ovarian fluid for culture and preservation of mammalian cells, comprising:

obtaining ovarian fluid from a fish; and culturing mammalian cells in media including a commercially defined medium and a nutrient medium;

wherein the nutrient medium includes the fish ovarian fluid.

3. A method of preserving living cells, comprising:

obtaining ovarian fluid from a fish;

isolating the living cells; and adding the fish ovarian fluid to the living cells.

* * * * *